(12) United States Patent
Ahmadi

(10) Patent No.: US 10,632,046 B2
(45) Date of Patent: Apr. 28, 2020

(54) MEDICATION GUIDANCE SYSTEM

(71) Applicant: Ahmad H. Ahmadi, Sugar Land, TX (US)

(72) Inventor: Ahmad H. Ahmadi, Sugar Land, TX (US)

( * ) Notice: Subject to any disclaimer, the term of this patent is extended or adjusted under 35 U.S.C. 154(b) by 0 days.

(21) Appl. No.: 16/375,533

(22) Filed: Apr. 4, 2019

(65) Prior Publication Data

US 2019/0224078 A1 Jul. 25, 2019

Related U.S. Application Data

(63) Continuation-in-part of application No. 14/746,081, filed on Jun. 22, 2015, now Pat. No. 10,285,904.

(51) Int. Cl.
| | |
|---|---|
| *A61J 7/04* | (2006.01) |
| *A61J 7/00* | (2006.01) |
| *G16H 20/13* | (2018.01) |
| *G07F 17/00* | (2006.01) |
| *A61J 1/03* | (2006.01) |
| *G01N 21/95* | (2006.01) |

(52) U.S. Cl.
CPC ........... *A61J 7/0418* (2015.05); *A61J 7/0076* (2013.01); *A61J 7/0436* (2015.05); *G07F 17/0092* (2013.01); *G16H 20/13* (2018.01); *A61J 1/035* (2013.01); *G01N 21/9508* (2013.01)

(58) Field of Classification Search
CPC ................................ A61J 7/0076; A61J 1/035
See application file for complete search history.

(56) References Cited

U.S. PATENT DOCUMENTS

| | | | | |
|---|---|---|---|---|
| 2010/0004782 | A1* | 1/2010 | Siegel | G16H 20/13 700/242 |
| 2010/0039682 | A1* | 2/2010 | Peot | H04N 1/00795 358/474 |
| 2012/0262039 | A1* | 10/2012 | Daugbjerg | G06F 19/3462 312/249.11 |
| 2013/0070090 | A1* | 3/2013 | Bufalini | G16H 20/13 348/143 |
| 2014/0172161 | A1* | 6/2014 | Norris | G07F 11/005 700/237 |

OTHER PUBLICATIONS

Polycom, RealPresence Practitioner Cart 8000, User's Guide, p/n 1793249, Revision C Mar. 2013 (Year: 2013).*

* cited by examiner

*Primary Examiner* — Evangeline Barr

(57) ABSTRACT

A medication guidance system that securely stored blister packs as well as keep accurate inventory of specific medication within the blister packs. The medication guidance system includes a drawer housing, a blister pack drawer, a latch mechanism, a plurality of light sources, a plurality of cameras, and a microcomputer. The drawer housing is the structural body and holds the blister pack drawer through a drawer hole. The blister pack drawer is slidably positioned within the drawer hole. The light sources and the cameras are positioned within the drawer housing and oriented towards the blister pack drawer to visually identify the contents placed within the blister pack drawer. The data taken by the cameras is graphically analyzed by the microcomputer for inventory and identification purposes. The latch mechanism is mechanically integrated in between the drawer housing and the blister pack drawer to manage access to the blister pack drawer.

19 Claims, 7 Drawing Sheets

MEDICATION GUIDANCE SYSTEM

FIELD OF THE INVENTION

The present invention relates generally to medication administration and storage. More specifically, the present invention is a medication guidance system for blister packs that notifies a user(s) of medication doses as well as automatically keeping track the inventory of the blister packs and their content.

BACKGROUND OF THE INVENTION

Advances in health care have helped to dramatically increase the lifespan of patients and their quality of life through the development of more effective treatments, medication, and medical technologies. However, one of the leading causes of medical patient readmission and patient fatalities is accidental patient or caregiver non-compliance with medication administration. Many patients often forget to take their medication, take too many doses of their medication, take their medication in an incorrect interval, or take the wrong medication. Additionally, patients do not keep a log of their medication intake. Incorrect administration of medication in the prescribed method can lead to serious medical complications, higher medical costs, and death. Most patients do not even keep a good medication intake log to help provide assistance in medical diagnosis. Even when patients use calendars, a caregiver, their own memory or other methods to help remind them to take a particular medication on time, there is no easy and automated way for them to verify if they are taking the correct medication or dosage. There is no easy way for a health care provider to track if their patients are taking their medication in the manner that they were prescribed. There is no easy and automated way for healthcare providers to immediately modify or cancel medication orders or for pharmaceutical manufactures to recall a medication after patient or caregivers have possession of the medication. Also, there is no easy or automated way for healthcare providers to alert patients who have taken a recalled pharmaceutical of the potential danger to the patients' lives.

Therefore, it is the object of the present invention to provide a medication guidance system that facilitates the proper administration of medication. The present invention is also useful for inventory management in hospital and other institutional settings. The present invention may be implemented as a cabinet or a mobile cart to store a multitude of medication in different compartments, wherein access to specific drawers of the cabinet is restricted to authorized personnel in order to control administration of the medication. When medication is administered to patients by authorized personnel, the administration of the medication doses is recorded by present invention and shared with the institution's database in order to maintain an inventory of the medication. This also prevents theft, as only authorized personnel are able to access medication within the present invention.

Furthermore, the present invention can be used to communicate with a designated caregiver (e.g. family member, nurse), physician, or pharmacist. This can be used to notify the caregiver, physician, or pharmacist when the user of the present invention does not acknowledge administration of a medication dose, cancels administration, or administers a dose that was cancelled by the physician or pharmacist. The present invention can also be used to request consultation or emergency consultation from the caregiver, physician, or pharmacist through the medication blister. Yet another communicable use of the present invention is the ability for the user to re-order medication by communicating with the physician or pharmacist through the medication blister cassette.

The invention also allows for remote inventory management unlike current methods which require authorized personnel to be present at the medication dispensing machines to manually check the inventory several times a day. It also notifies personnel if a diversion has occurred. Diversion of high value medications especially narcotics is a major financial, legal and safety burden on the health industry. By utilizing a computer vision analysis program, the present invention will immediately notify personnel if a case of diversion, such as unauthorized removal or removal of unauthorized number of medications has occurred thus bypassing human overseers.

DETAIL DESCRIPTIONS OF THE INVENTION

All illustrations of the drawings are for the purpose of describing selected versions of the present invention and are not intended to limit the scope of the present invention.

Figure 1:
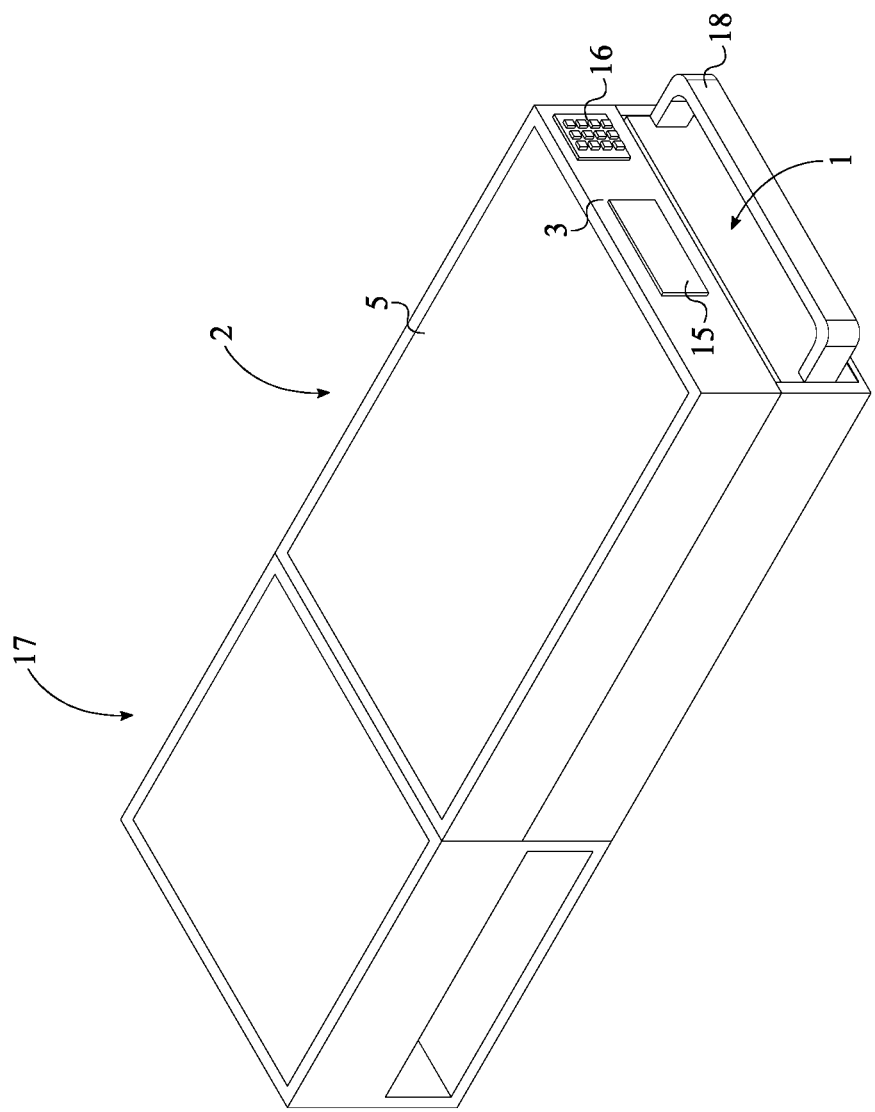
FIG. 1 is a perspective view of the present invention.
Figure 2:
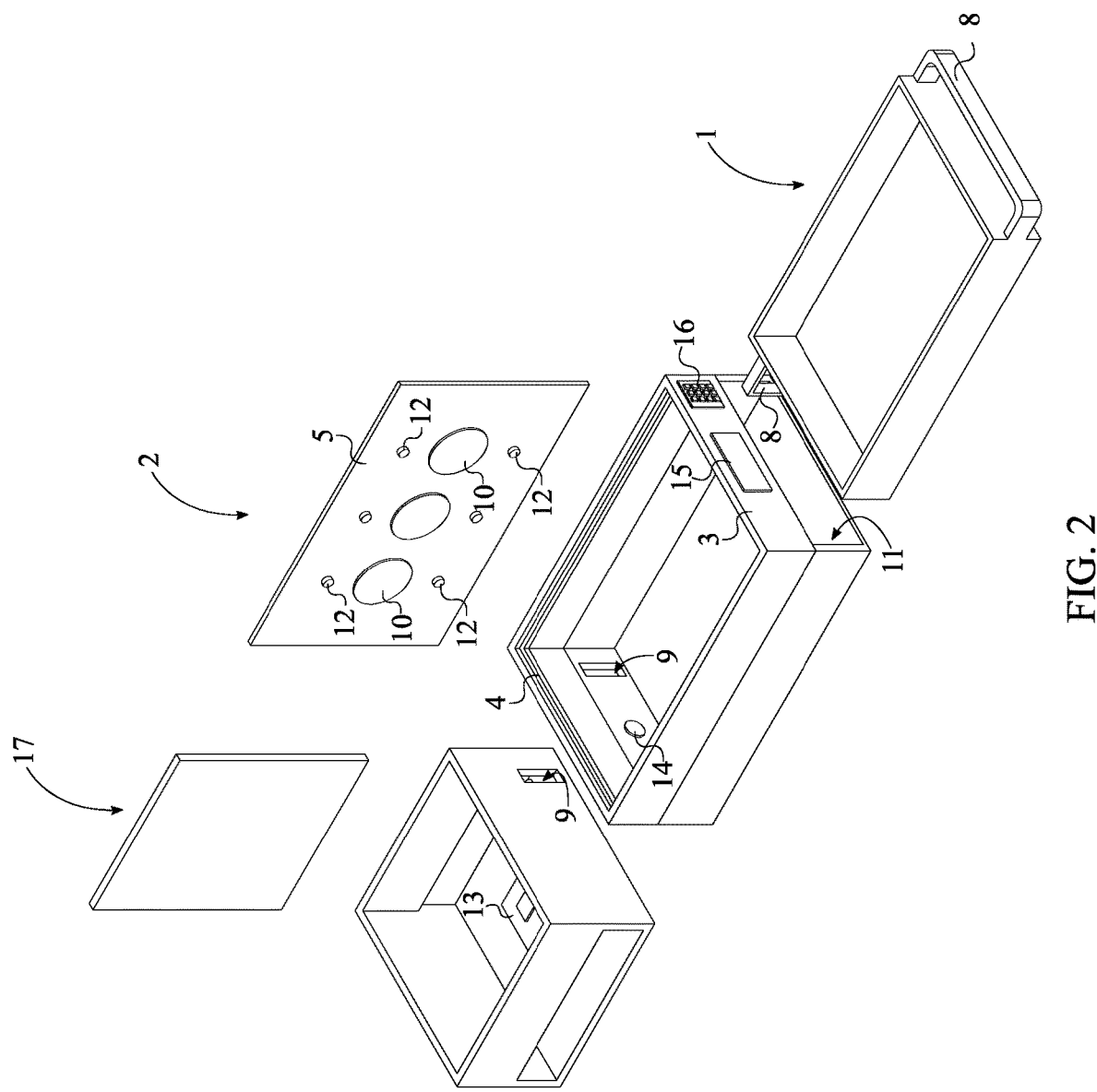
FIG. 2 is a perspective view of the present invention in an exploded state.

The present invention is a medication guidance system that facilitates the proper administration of medication as well as continuedly logging specific inventory of medication. Referring to FIG. 1 and FIG. 2, the present invention comprises a drawer housing 2, a blister pack drawer 1, a drawer hole 11, a latch mechanism 6, a plurality of light sources 10, a plurality of cameras 12, and a microcomputer 13. The drawer housing 2 acts as the main containment structure for the blister pack drawer 1, the plurality of light sources 10, and the plurality of cameras 12 to store, protect, and monitor medication within a blister pack. A blister pack is a preformed plastic packaging used for holding pharmaceuticals. The blister pack drawer 1 is a standard drawer that slides in and out of the drawer housing 2 to allow for a user to deposit and retrieve blister packs. The blister pack drawer 1 is attached to the drawer housing 2 through the drawer hole 11. The drawer hole 11 is sized complimentary to the blister pack drawer 1. Additionally, the drawer hole 11 normally traverses through a front panel 3 of the drawer housing 2. The blister pack drawer 1 is positioned within the drawer hole 11 and is slidably engaged along and within the drawer housing 2, similar to traditional drawer designs. The latch mechanism 6 serves as a lock and release mechanism between the blister pack drawer 1 and the drawer housing 2. The latch mechanism 6 is positioned adjacent to a rear panel 4 of the drawer housing 2 to attach the blister pack drawer 1 to the drawer housing 2. Additionally, the latch mechanism 6 is mechanically integrated in between the blister pack drawer 1 and the rear panel 4.

The plurality of light sources 10, the plurality of cameras 12, and the microcomputer 13 visually identify, track, and log the contents within a blister pack stored within the blister pack drawer 1. Specifically, each of the plurality of light sources 10 is a device that emits light to visually illuminate the internal space of the drawer housing 2. A variety of devices may be used for the plurality of light sources 10 including, but not limited to, light emitting diodes, incandescent bulbs, and other similar devices. The plurality of light sources 10 is positioned within the drawer housing 2. Additionally, each of the plurality of light sources 10 is internally mounted to the drawer housing 2. In the preferred embodiment of the present invention, the plurality of light sources 10 is adjacently mounted to a top panel 5 of the drawer housing 2, wherein each of the plurality of light sources 10 is oriented towards a bottom panel of the drawer housing 2; this configuration illuminates the internal space of the blister pack drawer 1 in result. Specifically, the plurality of light sources 10 is distributed about the top panel 5 with each of the plurality of lights sources being adjacently connected to the top panel 5. Furthermore, it is preferred that each of the plurality of light sources 10 is oriented towards the blister pack drawer 1. In alternative embodiments of the present invention, the plurality of light sources 10 may be distributed about the lateral sides of the drawer housing 2. In one embodiment of the present invention, the plurality of light sources 10 is distributed about the bottom panel, wherein the blister pack drawer 1 is semi-transparent or fully transparent such that the plurality of light sources 10 fully illuminate the contents within the blister pack drawer 1.

The plurality of cameras 12 captures images or video within the drawer housing 2, specifically of the contents within the blister pack drawer 1, to be analyzed by the microcomputer 13 or transferred to an external computer for image analysis. The plurality of cameras 12 is positioned within the drawer housing 2 with each of the plurality of cameras 12 being internally mounted to the drawer housing 2. Similar to the plurality of light sources 10, the plurality of cameras 12 is preferably positioned adjacent and mounted to the top panel 5. Specifically, the plurality of cameras 12 is distributed about the top panel 5 with each of the plurality of cameras 12 being adjacently connected to the top panel 5. This positions the plurality of cameras 12 at an offset height from the blister pack drawer 1, therefore increasing the coverage surface of the plurality of cameras 12. Additionally, each of the plurality of cameras 12 is oriented towards the blister pack drawer 1 to capture visual images/video of the contents within the blister pack drawer 1. The number within the plurality of cameras 12 is subject to change. Additionally, a variety of devices may be used for each of the plurality of cameras 12. In general, the plurality of light sources 10 illuminate the internal space of the blister pack drawer 1 while the plurality of cameras 12 record/capture the contents within said internal space. Additionally, the plurality of cameras 12 and the plurality of light sources 10 can be distributed about the bottom panel of the drawer housing 2 to capture images of the bottom surface of the blister pack drawer 1, wherein the blister pack drawer 1 is transparent.

Figure 7:
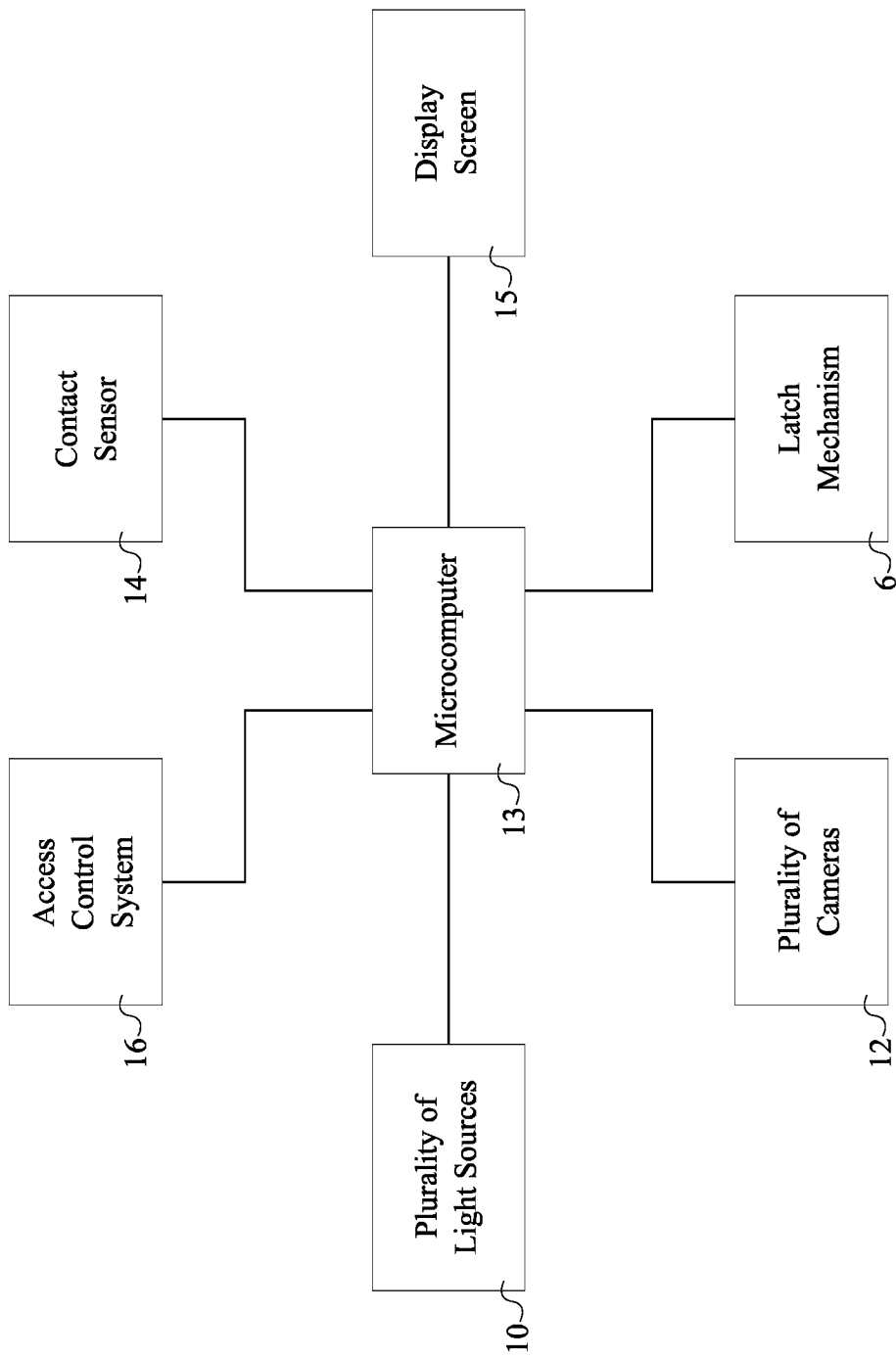
FIG. 7 is an electronic schematic diagram of the present invention.

The microcomputer 13 is mounted to the drawer housing 2 and controls the plurality of lights sources and the plurality of cameras 12. Specifically, the microcomputer 13 is electronically and electrically connected to each of the plurality of light sources 10 and each of the plurality of cameras 12 as seen in FIG. 7. In general, the plurality of light sources 10 illuminates the contents within the blister pack drawer 1 and the plurality of cameras 12 capture images and or video of the contents of the blister pack drawer 1. The microcomputer 13 receives the images and or video and graphically analyzes the images and or video to determine the exact content within the blister pack drawer 1. Alternatively, the captured images may be transmitted to a remote external storage and or server for archiving and image analysis. This may be accomplished through various image analysis software or by an authorized employee. Graphical analysis includes identifying the type of medication being stored, number of capsules remaining, access times of the blister pack drawer 1, and any other pertinent information required for keeping track of medicine within the blister pack drawer 1.

The information gathered and stored by the microcomputer 13 may be saved internally or may be transferred to an external server or computing device. This allows an administrative user to overview a multitude instances of the present invention, and thus track and overview medicine on a substantially large scale. For example, this allows an administrative user within a hospital to log and track medicine and monitor inventory for diversion for the whole facility with ease and efficiency, either locally or remotely. Referring to FIG. 2, the present invention also provides a means of displaying information about the contents within the blister pack drawer 1 and additionally provides a means of controlling who is able to access said contents. To achieve this, the present invention further comprises a display screen 15 and an access control system 16. The display screen 15 visually displays information to a user directly on the drawer housing 2. The display screen 15 is positioned adjacent to the front panel 3 for easy access. Additionally, the display device is adjacently connected to the front panel 3. The display screen 15 is electronically connected to the microcomputer 13 to receive the pertinent information necessary to display to the user. Any information gathered by the microcomputer 13 may be displayed by the display screen 15. Thus, the display screen 15 is electronically connected to the microcomputer 13. The access control system 16 is a security device designed to limit physical access to the blister pack drawer 1. The access control system 16 is positioned adjacent to the front panel 3 for easy access, specifically adjacent to the display screen 15. Additionally, the access control system 16 is adjacently connected to the front panel 3. The access control system 16 controls the status and state of the latching mechanism and therefore allows a user to open the blister pack drawer 1. For this, the access control system 16 is electronically connected to the latch mechanism 6 through the microcomputer 13. A variety of devices may be used as the access control system 16 including, but not limited to, a lock and key, an access pad, a finger print scanner, a retinal scanner, voice or face recognition, card scanner, radio frequency scanner, and other similar devices.

To further prevent unauthorized access to the present invention, the microcomputer 13 is mounted to the drawer housing 2 through a computer housing 17. This separates the microcomputer 13 from the internal space of the drawer housing 2. The computer housing 17 is positioned adjacent to the rear panel 4. Additionally, the computer housing 17 is adjacently mounted to the drawer housing 2. It is preferred that the height and width of the computer housing 17 matches that of the drawer housing 2 to allow a simple and stackable design. The microcomputer 13 is centrally positioned within the computer housing 17 and is mounted to the computer housing 17. The computer housing 17 may include an at least one vent hole for cooling purposes for the microcomputer 13.

Figure 3:
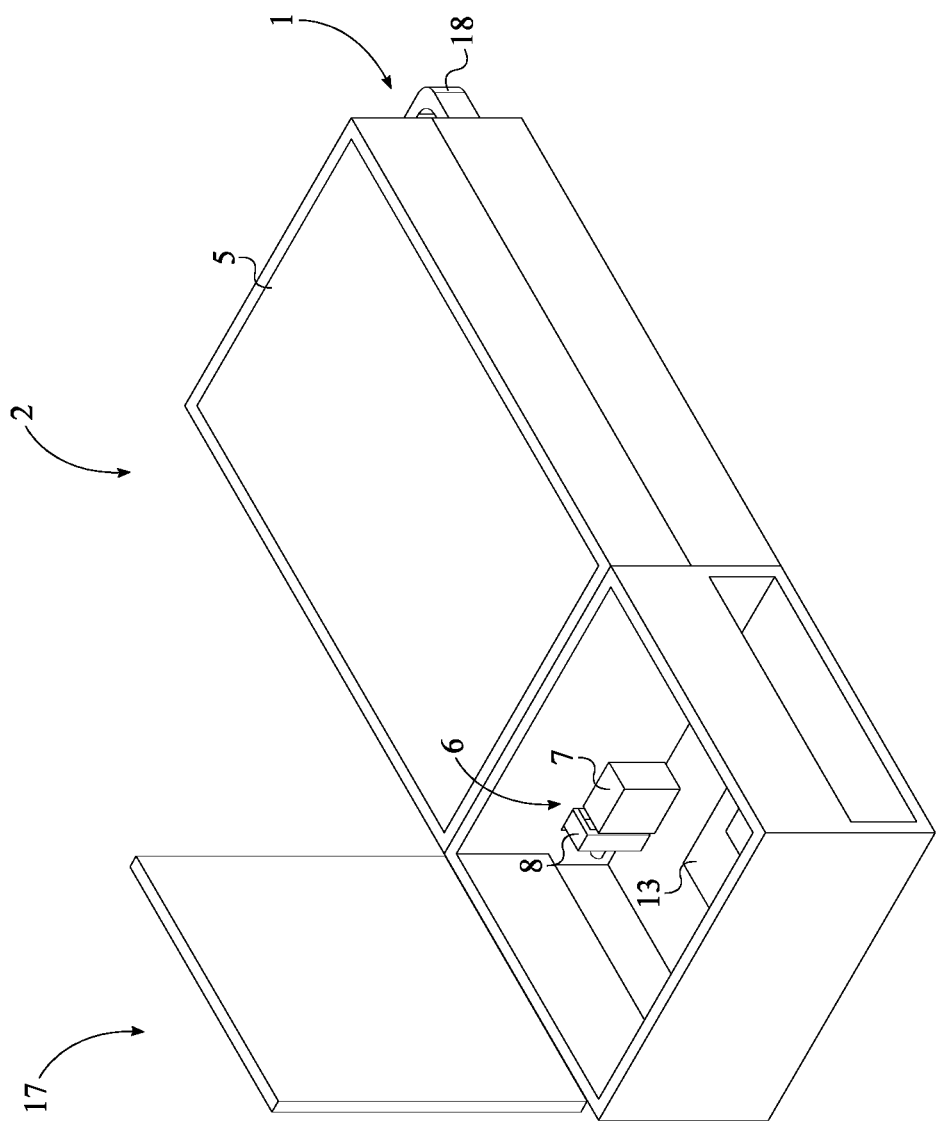
FIG. 3 is an alternative perspective view of the present invention in a partially exploded state.
Figure 4:
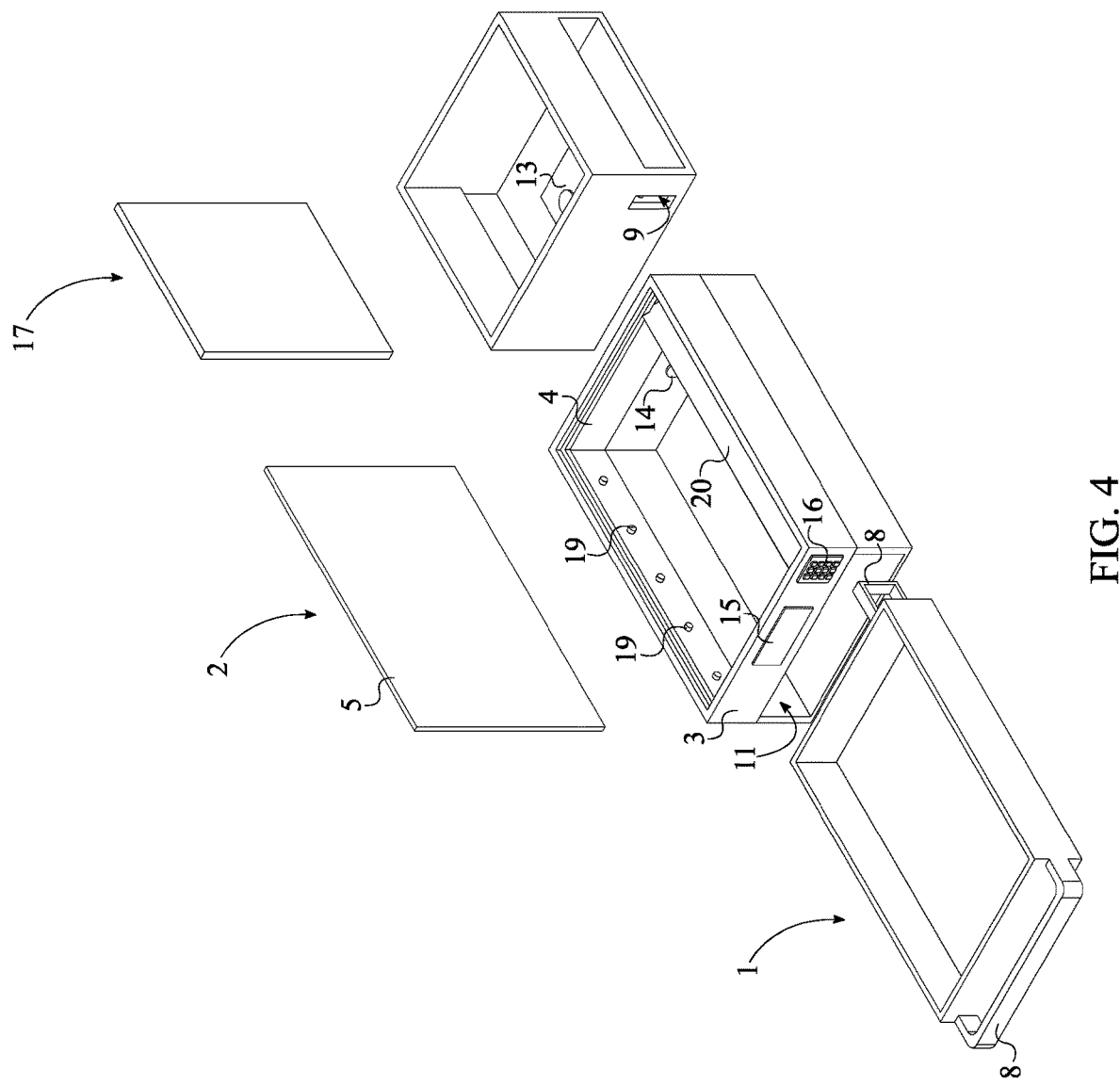
FIG. 4 is an alternative perspective view of an alternative embodiment of the present invention in an exploded state.

Additionally, the computer housing 17 is used to house a portion of the latch mechanism 6 as seen in FIG. 3. For this, the latch mechanism 6 comprises a solenoid latch 7, a U-shaped interlocking portion 8, and a latch hole 9. The solenoid latch 7 is an electromagnetic actuator that extends and retracts a locking pin to interlock with the U-shaped interlocking portion 8. The solenoid latch 7 is mounted within the computer housing 17 to prevent tampering to the latch mechanism 6. The U-shaped interlocking portion 8 is perpendicularly and adjacently connected to the blister pack drawer 1. When the blister pack drawer 1 is fully positioned within the drawer housing 2, the U-shaped interlocking portion 8 is positioned adjacent to the rear panel 4. Specifically, the U-shaped interlocking portion 8 is designed to traverse through the rear panel 4 through the latch hole 9. The latch hole 9 connects the internal space of the computer housing 17 with the internal space of the drawer housing 2. Referring to FIG. 4, the latch hole 9 normally traverses through the rear panel 4 and into the computer housing 17. The solenoid latch 7 is thus positioned adjacent to the latch hole 9. To secure the blister pack drawer 1 within the drawer housing 2, the blister pack drawer 1 is positioned within the drawer housing 2 until the U-shaped interlocking portion 8 is positioned within the latch hole 9. The solenoid latch 7 is then mechanically engaged to the U-shaped interlocking portion 8 to secure the blister pack drawer 1 within the drawer housing 2. Alternatively, the location and means of the latch/mechanism 6 can be changed; for example a magnetic lock may be used.

A contact sensor 14 detects whether or not the blister pack drawer 1 is positioned within the drawer housing 2. The contact sensor 14 is a device that measures the direct presence of an object, specifically the blister pack drawer 1. The contact sensor 14 is positioned within the drawer housing 2 and is mounted to the rear panel 4, adjacent to the blister pack drawer 1. When the blister pack drawer 1 is fully positioned within the drawer housing 2, the blister pack drawer 1 presses against the contact sensor 14, opposite the rear panel 4. This activates the contact sensor 14 and signals to the microcomputer 13 that the blister pack drawer 1 is fully positioned within the drawer housing 2. For this, the contact sensor 14 is electronically connected to the microcomputer 13. The specific position of the blister pack drawer 1 determines if the latch mechanism 6 is capable of being engaged or disengaged.

Referring to FIG. 2, the present invention further comprises a handle 18 for the blister pack drawer 1. The handle 18 acts as the grasping element for user to open and close the blister pack drawer 1. The handle 18 is a U-shaped structure that is externally positioned to the blister pack drawer 1. Additionally, the handle 18 is adjacently connected to the blister pack drawer 1, adjacent to the front panel 3.

Figure 6:
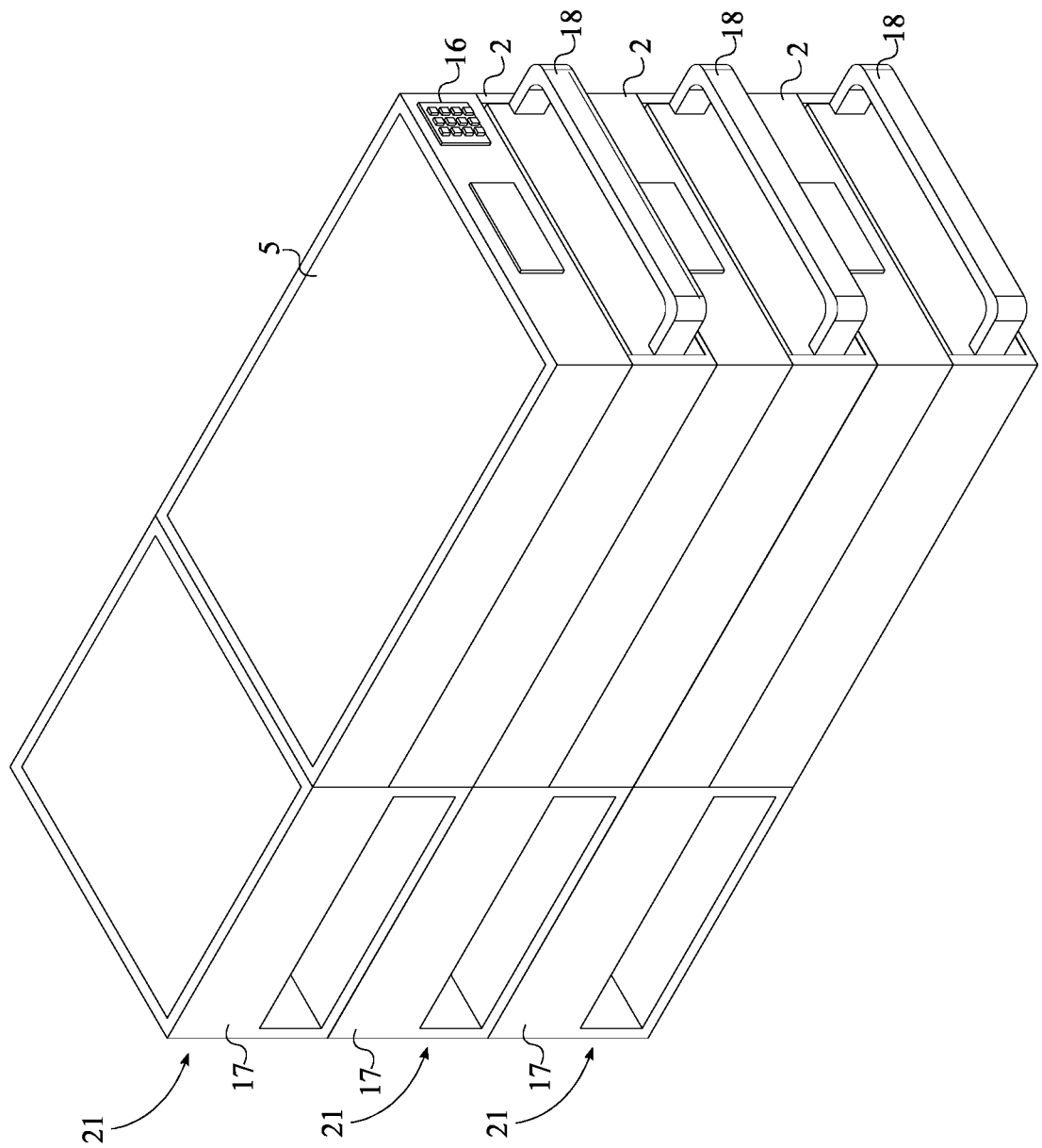
FIG. 6 is a perspective view of the present invention.

Referring to FIG. 6, the present invention may be implemented as a plurality of medication storage units 21. In this embodiment, each of the plurality of medication storage units 21 comprises the blister pack drawer 1, the drawer housing 2, the latch mechanism 6, the plurality of light sources 10, the drawer hole 11, the contact sensor 14, the display screen 15, the computer housing 17, the handle 18, the plurality of cameras 12, and the microcomputer 13. In such case, only a single instance of the access control system 16 would be utilized for the plurality of medication storage units 21. This provides a means of storing a large quantity of medicine, each with a dedicated secure location. The plurality of medication storage unit is serially distributed with each other to yield a cabinet-type configuration. Each of the plurality of medication storage units 21 may be used to store specific medication, medication for a specific patient, and or medication for specific doctors. Thus, medicine inventory may be logged and categorized with increased accuracy. This also prevents theft, as only authorized personnel are able to access any of the plurality of medication storage units 21.

Figure 5:
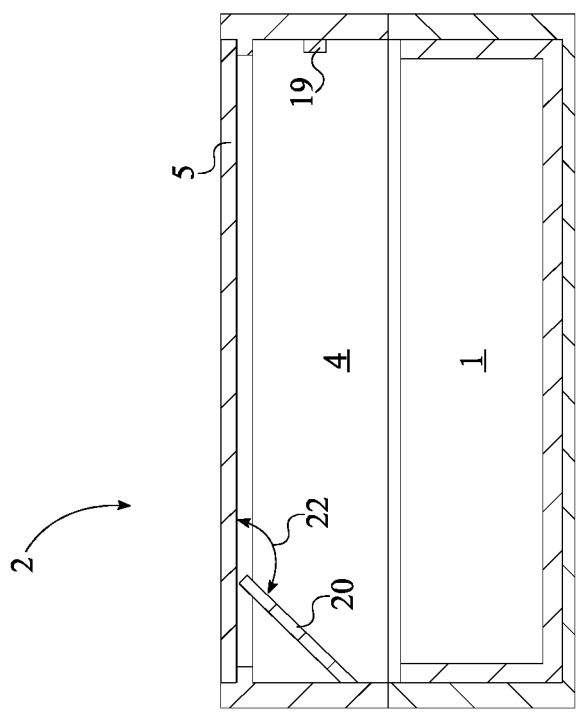
FIG. 5 is a cross-sectional view of the alternative embodiment of the present invention.

Referring to FIG. 4 and FIG. 5, in one embodiment of the present invention, a plurality of lateral cameras 19 in conjunction with an at least one mirror 20 may be used to visually capture the contents within the blister pack drawer 1. The mirror 20 is positioned to reflect an image of the internal space of the blister pack drawer 1. The plurality of lateral cameras 19 is oriented towards the mirror 20 to capture the reflected image. Specifically, the plurality of lateral cameras 19 and the mirror 20 are positioned within the drawer housing 2; wherein the plurality of lateral cameras 19 and the mirror 20 are positioned opposite to each other, across the drawer housing 2 as seen in FIG. 5. Each of the plurality of lateral cameras 19 is adjacently connected to the drawer housing 2, adjacent to the top panel 5. Additionally, the mirror 20 is adjacently mounted to the top panel 5 at an obtuse angle 22 such that light from the blister pack drawer 1 will hit the mirror 20 and reflect towards the plurality of lateral cameras 19. This provides an alternative means of filming the contents within the blister pack drawer 1. Similar to the plurality of cameras 12, each of the plurality of lateral cameras 19 is electronically connected to the microcomputer 13.

In another embodiment of the present invention, an at least one internal camera and a plurality of optical conduits to visually capture the contents with the blister pack drawer 1. Each of the plurality of optical conduits can be solid, hollow tube or fiber optic cable that comprises a multitude of optical fibers that transmit light between ends. In this embodiment, a first end of the each of the plurality of optical conduits is mounted within the drawer housing 2 and oriented towards the bottom panel, i.e. the blister pack drawer 1. A second end of each of the plurality of optical conduits is mounted adjacent to the internal camera. The internal camera captures the light from the plurality of optical conduits and transfers said image to the microcomputer 13. The internal camera may be mounted anywhere within the present invention. Although, it is preferred that the internal camera is mounted within the computer housing 17. Additionally, the internal camera is electronically connected to the microcomputer 13 to transfer images/video of the contents of the blister pack drawer 1 to the microcomputer 13 for analysis.

Although the invention has been explained in relation to its preferred embodiment, it is to be understood that many other possible modifications and variations can be made without departing from the spirit and scope of the invention as hereinafter claimed.

What is claimed is:
1. A medication guidance system comprising:
a blister pack drawer;
a drawer housing;
a latch mechanism;
a plurality of light sources;
a drawer hole;
a plurality of first cameras;
a microcomputer;
the drawer housing comprising a top panel, a bottom panel, a front panel and a rear panel;
the drawer hole normally traversing through the front panel;

the blister pack drawer being positioned within the drawer hole;

the blister pack drawer being slidably engaged along and within the drawer housing;

the plurality of light sources and the plurality of first cameras being positioned within the drawer housing;

the plurality of light sources being internally mounted to the drawer housing;

the plurality of first cameras being internally mounted to the drawer housing;

the latch mechanism being positioned adjacent to the rear panel;

the latch mechanism being mechanically integrated in between the blister pack drawer and the rear panel;

the microcomputer being mounted to the drawer housing;

a plurality of optical conduits;

the plurality of optical conduits being mounted within the drawer housing;

a first end of each of the plurality of optical conduits being oriented towards the bottom panel;

a second end of each of the plurality of optical conduits being adjacently located to each of the plurality of first cameras;

the blister pack drawer being transparent;

a plurality of second cameras;

the plurality of second cameras being internally mounted to the drawer housing;

the plurality of second cameras being distributed on the bottom panel;

the plurality of second cameras being oriented towards the top panel; and the microcomputer being electronically connected to the plurality of light sources, the plurality of first cameras, the plurality of second cameras and the latch mechanism.

2. The medication guidance system as claimed in claim 1 comprising:

a contact sensor;

the contact sensor being positioned within the drawer housing;

the contact sensor being mounted to the rear panel, adjacent to the blister pack drawer;

the blister pack drawer being pressed against the contact sensor, opposite the rear panel; and the contact sensor being electronically connected to the microcomputer.

3. The medication guidance system as claimed in claim 1 comprising:

a display screen;

the display screen being positioned adjacent to the front panel;

the display screen being connected to the front panel; and the display screen being electronically connected to the microcomputer.

4. The medication guidance system as claimed in claim 1 comprising:

an access control system;

the access control system being positioned adjacent to the front panel;

the access control system being connected to the front panel; and the access control system being electronically connected to the latch mechanism through the microcomputer.

5. The medication guidance system as claimed in claim 1 comprising:

a computer housing;

the latch mechanism comprising a solenoid latch, a U-shaped interlocking portion, and a latch hole;

the computer housing being positioned adjacent to the rear panel;

the computer housing being mounted to the drawer housing;

the microcomputer being mounted within the computer housing;

the latch hole normally traversing through the rear panel and into the computer housing;

the solenoid latch being mounted within the computer housing, adjacent to the latch hole;

the U-shaped interlocking portion being perpendicularly connected to the blister pack drawer;

the U-shaped interlocking portion being positioned within the latch hole; and the solenoid latch being mechanically engaged to the U-shaped interlocking portion.

6. The medication guidance system as claimed in claim 1 comprising:

a handle;

the handle being externally positioned to the blister pack drawer; and the handle being connected to the blister pack drawer, adjacent to the front panel.

7. The medication guidance system as claimed in claim 1 comprising:

the plurality of first cameras being distributed on the top panel;

the plurality of first cameras being connected to the top panel; and the plurality of first cameras being oriented towards the blister pack drawer.

8. The medication guidance system as claimed in claim 1 comprising:

the plurality of light sources being distributed on the top panel;

the plurality of light sources being connected to the top panel; and the plurality of light sources being oriented towards the blister pack drawer.

9. The medication guidance system as claimed in claim 1 comprising:

a plurality of lateral cameras;

at least one mirror;

the plurality of lateral cameras and the mirror being positioned within the drawer housing;

the plurality of lateral cameras and the mirror being positioned opposite to each other, across the drawer housing;

the plurality of lateral cameras being connected to the drawer housing, adjacent to the top panel;

the mirror being mounted to the top panel at an obtuse angle; and the plurality of lateral cameras being electronically connected to the microcomputer.

10. The medication guidance system as claimed in claim 1 comprising:

a plurality of medication storage units;

each of the plurality of medication storage units comprising the blister pack drawer, the drawer housing, the latch mechanism, the plurality of light sources, the drawer hole, the plurality of first cameras, and the microcomputer; and the plurality of medication storage units being serially distributed with each other.

11. A medication guidance system comprising:

a blister pack drawer;

a drawer housing;
a latch mechanism;
a plurality of light sources;
a drawer hole;
a plurality of first cameras;
a microcomputer;
a computer housing;
the latch mechanism comprising a solenoid latch, a U-shaped interlocking portion, and a latch hole;
the drawer housing comprising a top panel, a bottom panel, a front panel and a rear panel;
the drawer hole normally traversing through the front panel;
the blister pack drawer being positioned within the drawer hole;
the blister pack drawer being slidably engaged along and within the drawer housing;
the plurality of light sources and the plurality of first cameras being positioned within the drawer housing;
the plurality of light sources being internally mounted to the drawer housing;
the plurality of first cameras being internally mounted to the drawer housing;
the latch mechanism being positioned adjacent to the rear panel;
the latch mechanism being mechanically integrated in between the blister pack drawer and the rear panel;
the microcomputer being mounted to the drawer housing;
the computer housing being positioned adjacent to the rear panel;
the computer housing being mounted to the drawer housing;
the microcomputer being mounted within the computer housing;
the latch hole normally traversing through the rear panel and into the computer housing;
the solenoid latch being mounted within the computer housing, adjacent to the latch hole;
the U-shaped interlocking portion being perpendicularly connected to the blister pack drawer;
the U-shaped interlocking portion being positioned within the latch hole;
the solenoid latch being mechanically engaged to the U-shaped interlocking portion;
a plurality of optical conduits;
the plurality of optical conduits being mounted within the drawer housing;
a first end of each of the plurality of optical conduits being oriented towards the bottom panel;
a second end of each of the plurality of optical conduits being adjacently located to each of the plurality of first cameras;
the blister pack drawer being transparent;
a plurality of second cameras;
the plurality of second cameras being internally mounted to the drawer housing;
the plurality of second cameras being distributed on the bottom panel;
the plurality of second cameras being oriented towards the top panel; and
the microcomputer being electronically connected to the plurality of light sources, the plurality of first cameras, the plurality of second cameras and the latch mechanism.

12. The medication guidance system as claimed in claim 11 comprising:
a contact sensor;
the contact sensor being positioned within the drawer housing;
the contact sensor being mounted to the rear panel, adjacent to the blister pack drawer;
the blister pack drawer being pressed against the contact sensor, opposite the rear panel; and
the contact sensor being electronically connected to the microcomputer.

13. The medication guidance system as claimed in claim 11 comprising:
a display screen;
the display screen being positioned adjacent to the front panel;
the display screen being connected to the front panel; and
the display screen being electronically connected to the microcomputer.

14. The medication guidance system as claimed in claim 11 comprising:
an access control system;
the access control system being positioned adjacent to the front panel;
the access control system being connected to the front panel; and
the access control system being electronically connected to the latch mechanism through the microcomputer.

15. The medication guidance system as claimed in claim 11 comprising:
a handle;
the handle being externally positioned to the blister pack drawer; and
the handle being connected to the blister pack drawer, adjacent to the front panel.

16. The medication guidance system as claimed in claim 11 comprising:
the plurality of first cameras being distributed on the top panel;
the plurality of first cameras being connected to the top panel; and
the plurality of first cameras being oriented towards the blister pack drawer.

17. The medication guidance system as claimed in claim 11 comprising:
the plurality of light sources being distributed on the top panel;
the plurality of light sources being connected to the top panel; and
the plurality of light sources being oriented towards the blister pack drawer.

18. The medication guidance system as claimed in claim 11 comprising:
a plurality of lateral cameras;
at least one mirror;
the plurality of lateral cameras and the mirror being positioned within the drawer housing;
the plurality of lateral cameras and the mirror being positioned opposite to each other, across the drawer housing;
the plurality of lateral cameras being connected to the drawer housing, adjacent to the top panel;
the mirror being mounted to the top panel at an obtuse angle; and
the plurality of lateral cameras being electronically connected to the microcomputer.

19. The medication guidance system as claimed in claim 11 comprising:
a plurality of medication storage units;

each of the plurality of medication storage units comprising the blister pack drawer, the drawer housing, the latch mechanism, the plurality of light sources, the drawer hole, the plurality of first cameras, and the microcomputer; and
the plurality of medication storage units being serially distributed with each other.

* * * * *